United States Patent
Slocik et al.

(10) Patent No.: US 11,058,770 B1
(45) Date of Patent: Jul. 13, 2021

(54) ULTRASTABLE ANTIBODY IONIC LIQUIDS

(71) Applicant: Government of the United States, as represented by the Secretary of the Air Force, Wright-Patterson AFB, OH (US)

(72) Inventors: Joseph M Slocik, Dayton, OH (US); Rajesh R. Naik, Centerville, OH (US); Patrick B Dennis, Cincinnati, OH (US)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 220 days.

(21) Appl. No.: 16/256,029

(22) Filed: Jan. 24, 2019

(51) Int. Cl.
*A61K 39/395* (2006.01)
*A61K 47/20* (2006.01)

(52) U.S. Cl.
CPC .... *A61K 39/39591* (2013.01); *A61K 39/3955* (2013.01); *A61K 47/20* (2013.01)

(58) Field of Classification Search
CPC .......... A61K 39/39591; A61K 39/3955; A61K 47/20
See application file for complete search history.

(56) References Cited

FOREIGN PATENT DOCUMENTS

| WO | WO-2015038811 A2 * | 3/2015 | .............. A61P 43/00 |
| WO | WO-2017070364 A1 * | 4/2017 | ....... G01N 33/56966 |

OTHER PUBLICATIONS

Floyd et al., Protein Engineering, Design & Selection 22:159-168 (Year: 2009).*
Edwards et al., J Mol Biol. 334(1): 103-118 (Year: 2003).*
Rudikoffetal., Proc Natl Acad Sci USA 79: 1979-1983 (Year: 1982).*
Perriman A.W. et al., Solvent-Free Protein Liquids and Liquid Crystals, Angew. Chem. Int. Ed., 2009, vol. 48, 6242-6246.

* cited by examiner

*Primary Examiner* — Phuong Huynh
(74) *Attorney, Agent, or Firm* — AFMCLO/JAZ; Timothy M. Barlow

(57) ABSTRACT

A stable protein ionic liquid, comprising an anti-hemoglobin cation/anion pair. The anti-hemoglobin cation/anion pair may be an anionic polymer of poly(ethylene glycol) 4-nonylphenyl 3-sulfopropyl ether. The anti-hemoglobin cation/anion pair may further comprise a cationized anti-hemoglobin antibody, single-chain antibodies from camelids, antibody fragments, polyclonal Anti-horse spleen ferritin antibodies, monoclonal Anti-Flag antibodies, monoclonal Anti-HRP2 to *Plasmodium falciparum*, polyclonal Anti-neuropeptide Y, polyclonal Anti-human troponin, isotypes of antibodies, or combinations of multiple antibodies.

2 Claims, 7 Drawing Sheets

ULTRASTABLE ANTIBODY IONIC LIQUIDS

RIGHTS OF THE GOVERNMENT

The invention described herein may be manufactured and used by or for the Government of the United States for all governmental purposes without the payment of any royalty.

Pursuant to 37 C.F.R. § 1.78(a)(4), this application claims the benefit of and priority to prior filed Non-Provisional application Ser. No. 15/440,832, filed 23 Feb. 2017, now U.S. Pat. No. 10,463,733, and Provisional Application Ser. No. 62/403,774, filed 4 Oct. 2016, which are expressly incorporated herein by reference.

FIELD OF THE INVENTION

The present invention relates generally to ultra-stable, water-free biological materials and, more particularly, to ultra-stable, heat-resistant, biologically active, water-free protein ionic liquids that do not require refrigeration.

BACKGROUND OF THE INVENTION

Most biological materials (i.e. proteins and antibodies) thrive in aqueous environments and physiological conditions (neutral pH—between 6-8, ambient temperatures 25-37° C.) in order to perform their biological function. Water is used for stabilizing some biomolecular structures through hydrogen bonding, providing proton donors/acceptors, regulating binding interactions, and controlling molecular dynamics. Conversely, water is also detrimental to biomolecular structure and function by increasing the rate of hydrolysis and oxidation, destabilizing protein structure, and increasing the susceptibility/sensitivity to elevated temperatures. In total, this results in denaturation, proteolytic degradation, decomposition, and short shelf-lives.

In order to counteract the effects of water and limit decomposition, current biomolecules, e.g. proteins and antibodies, may require constant refrigeration during storage, handling, and transport in order to preserve structure, functionality, and biological activity. Generally, antibodies in water may be stable for up to one month when stored at about 4° C. and up to one year when stored in 25% glycerol at −20° C. The presence of water in a biological solution will typically result in hydrolysis, even if the temperature is reduced or the solution is frozen. Water promotes hydrogen bonding, intramolecular interactions, stabilizes the antibody structure, facilitates mass transport and diffusion of products, and regulates binding interactions. Water also increases the sensitivity of the antibodies to elevated temperatures, destabilizes protein structures, increases hydrolysis and oxidation rates, reduces shelf lives, and promotes unfolding/denaturation. Consequently, the exclusion of water from antibody preparations is highly appealing and offers a means towards reducing protein degradation, increasing stability, enabling refrigeration-free storage and handling, and significantly increasing shelf-lives. In addition, even if freezing or refrigeration are acceptable alternatives, many places around the world have no available electricity to power refrigeration equipment. The half-life of unrefrigerated antibodies may be as short as 2 days.

SUMMARY OF THE INVENTION

The present invention overcomes the foregoing problems and other shortcomings, drawbacks, and challenges of making stable biologically-active materials, such as proteins and antibodies. While the invention will be described in connection with certain embodiments, it will be understood that the invention is not limited to these embodiments. To the contrary, this invention includes all alternatives, modifications, and equivalents as may be included within the spirit and scope of the present invention.

Based on the numerous drawbacks associated with water in antibody solutions, see above, the aim of this invention, in one embodiment, is the removal of most or all water, i.e. at least 95% water removed, without disrupting the protein/antibody structure and intramolecular interactions/functions. The proteins and/or antibodies are chemically modified into an ionic liquid, but when antibodies are used the modified antibodies maintain high antigen recognition, specificity, and binding affinity, e.g., the modified antibodies maintain picomolar (pM) dissociation constants (KD) about equal to those of native, unmodified antibodies. With regard to binding affinity, this means that the antigens bind strongly to the modified antibodies.

"Water-free" (as defined herein) protein liquids feature the simplicity of traditional inorganic ionic liquids (facile synthesis, ability to tune properties through choice of cation and anion pair, and stability), but display the complexity and functionality of highly active proteins, e.g. antibodies. Because the protein liquids have most or all of the water removed, they are stable liquids, resistant to extreme temperatures (>100° C.), able to maintain biological recognition activity, and exhibit much longer shelf-lives without the need for refrigeration.

According to one embodiment of the present invention a method for creating a stable protein ionic liquid, comprises: (a) cationizing aqueous proteins by addition of an excess of a positively-charge crosslinker in the presence of a coupling agent; (b) purifying the cationized proteins; (c) titrating the cationized proteins with a corresponding biologically-compatible counter anionic polymer to create at least one antibody cation/anion pair in aqueous solution until the antibody cation/anion pair solution becomes negative by zeta potential measurement; (d) dialyzing the at least one protein cation/anion pair in water at least once to remove excess anionic polymer using at least one molecular weight cutoff 7000 dialysis membrane; (e) lyophilizing the at least one protein cation/anion pair to remove most of the water, forming a lyophilized solid; and (f) heating the lyophilized solid until a protein ionic liquid is generated. In cationizing the aqueous proteins, a minimum zeta potential value of +5 mV is desired for cationization. In titrating the cationized antibodies, the negative zeta potential is meant below 0 mV to about −1 mV by zeta potential. A negative zeta potential of the titrated cationized antibodies ensures that there is a minor excess of anion but that the positive charges are equally balanced. Heating of the lyophilized solid may be done on a hotplate, in a temperature controlled water bath, or an oven at about 27-50° C., for example. This provides the advantage of producing stable, heat-resistant, biologically active protein ionic liquids that do not require refrigeration. In one embodiment of the present invention, the protein ionic liquid is a viscous, clear liquid. Antibodies may include but are not limited to IgG, IgY, IgM, and other proteins or negatively-charged molecules may also be rendered stable according to the teachings herein.

According to a first variation, the method for creating a stable protein ionic liquid further comprises purifying the cationized proteins from excess coupling reagents by dialysis in water. This provides the advantage of obtaining a pure protein sample composed of only proteins modified with positive charges.

According to another variation, the method for creating a stable protein ionic liquid further comprises cationizing aqueous proteins by addition of an excess of or a stoichiometric amount of N,N-dimethyl-1,3-propanediamine cross-linker in the presence of 1-ethyl-3-(3-dimethylaminopropyl) carbodiimide (EDC) coupling reagent.

According to a further variation, the method for creating a stable protein ionic liquid further comprises cationizing aqueous proteins by addition of an excess of or a stoichiometric amount of 2-(dimethylamino) ethanethiol crosslinker in the presence of succinimidyl iodoacetate (SIA) coupling agent.

According to a further variation, the method for creating a stable protein ionic liquid further comprises cationizing aqueous proteins by addition of an excess of or a stoichiometric amount of 2-(dimethylamino) ethanethiol crosslinker in the presence of N-(p-maleimidophenyl) isocyanate (PMPI) coupling agent.

According to another variation, the method for creating a stable protein ionic liquid further comprises performing the dialysis with at least one membrane with a molecular weight cutoff (MWCO) of about 7000 g/mol. According to a further variation, the method for creating a stable protein ionic liquid further comprises performing the dialysis with at least one membrane with a molecular weight cutoff of between about 6000-15,000 g/mol. In one embodiment this membrane may remove a plurality of contaminants and excess reagents from the modified proteins that are below a molecular weight, e.g. 7000 g/mol. A molecular weight of at least about 7000 g/mol typically ensures that all coupling reagents, positively-charged cross-linker, and buffer salts are separated from cationized proteins. About 7000 g/mol may be the lower limits for this dialysis, however, the membrane could be as large as 15,000 g/mol, but at the risk of losing proteins through the larger membrane.

According to a further variation, the method for creating a water-free ultra-stable protein ionic liquid further comprises confirming the cationizing of the aqueous proteins by measuring a positive zeta potential value. The zeta potential may be between about 0 mV and +5 mV. This provides the advantage of determining the number of positive charges added to the protein.

According to another variation, the method for creating a stable protein ionic liquid further comprises titrating the cationized proteins with the corresponding biologically-compatible counter anionic polymer of poly(ethylene glycol) 4-nonylphenyl 3-suopropyl ether, i.e. $C_9H_{19}C_6H_4$—$(OCH_2CH_2)_{20}O(CH_2)_3SO_3$. In other embodiments the counter anion polymer may be biologically-derived DL-Lactate, biologically-derived linolenic acid, phospholipids, fatty acids, the conjugate base form of amino acids (i.e. deprotonated and negatively charged), any biologically-derived singly-charged anion with low melting points (e.g. between about 5-30° C.). This provides the advantage of balancing the positive charges on the protein with negative charges of the anion to form the ionic salt form of the protein.

According to a further variation, the method for creating a stable protein ionic liquid further comprises heating the lyophilized solid to about 50° C. to generate the protein ionic liquid. This provides the advantage of melting the protein ionic salt to form a viscous water-free liquid without deactivating the protein.

According to another embodiment of the invention, the protein may be an antibody.

According to another variation, the method for creating a stable protein ionic liquid further comprises heating the protein ionic liquid at about 100° C. for about 2 hours; and testing the protein ionic liquid for antibody recognition of a corresponding antigen, when the protein is an antibody. In one embodiment, the testing may be done using a dot blot assay on a nitrocellulose membrane. In a further embodiment, the heating may be between about 75° C. and about 150° C. and/or may be between 1 and 3 hours. This provides the advantage of evaluating the temperature stability of the protein/antibody ionic liquid at extreme temperatures by directly measuring binding activity of the antibody for an antigen.

According to a further variation, the protein is an anti-hemoglobin antibody, polyclonal anti-horse spleen ferritin antibodies, monoclonal Anti-Flag antibodies, monoclonal Anti-HRP2 to *Plasmodium falciparum*, polyclonal Anti-neuropeptide Y, polyclonal Anti-human troponin, and all antibody isotypes, e.g. IgY, IgG, IgM, IgE, etc.

In addition, a dye, such as an IR active dye, may be combined with blood-typing antibody solutions via conjugation of an amine reactive dye, e.g., Anti-A ionic liquid, such that blood typing may be accomplished without visible light using night vision goggles to determine blood type via the hemagluttination of red blood cells, a tremendous boon to soldiers and field medics in hazardous regions. Other variations may be useful for lateral flow assays, enzyme-linked immunosorbent assays (ELISA), anti-venom/anti-toxin therapeutics, immunotherapy, vaccines, anti-virals, detection of chemical, biological, nuclear, environmental and radioactive agents, and may be applied to other biologically-important proteins whether negatively or positively charged, e.g., insulin.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

The following examples illustrate particular properties and advantages of some of the embodiments of the present invention. Furthermore, these are examples of reduction to practice of the present invention and confirmation that the principles described in the present invention are therefore valid but should not be construed as in any way limiting the scope of the invention.

This invention exploits the physical properties of ionic liquids and the biological recognition of antigen-specific antibodies to create a stable and heat-resistant antibody protein ionic liquid that exhibits refrigeration-free storage and handling, which makes it suitable for use or storage at typical room temperatures. However, such a process has numerous obstacles to overcome because antibodies and many other proteins are negatively charged. This makes such proteins and antibodies difficult to ionically combine with anions. In order to create an ionic liquid with antibodies, the antibodies' charge must be made more positive. Antibodies have a great number of negative sites (e.g. carboxyl groups, —COOH; amine groups —NH$_2$; hydroxyl groups, —OH) to address, but in order to maintain the activity of the antibody the cationization process should not be too aggressive. In short, too few positive charges yields an antibody that does not function correctly as a salt. Too many positive charges yields an antibody with diminished biological activity, i.e. once the antibody's non-acid (general) amino acids are coupled the antibody loses its specificity and its usefulness.

Figure 1:
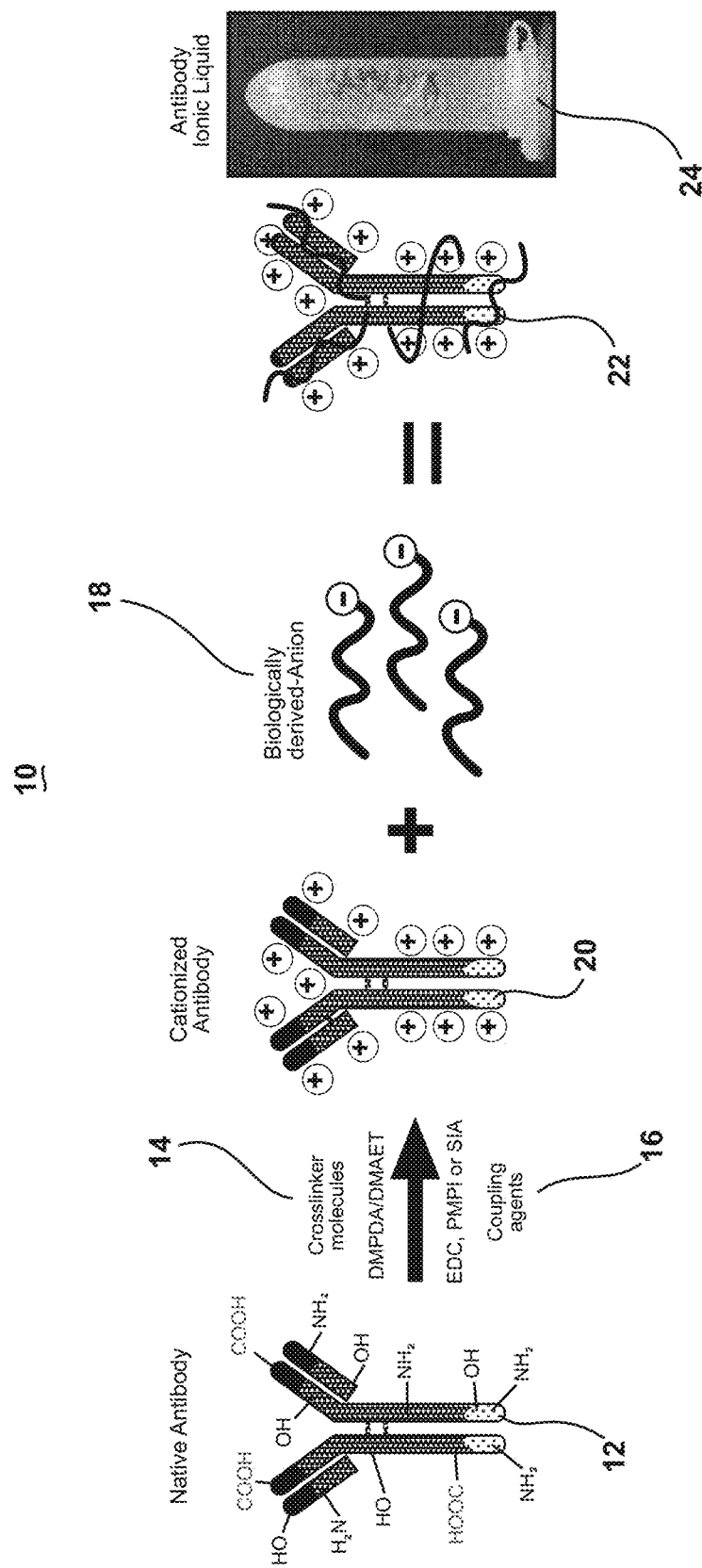
FIG. 1 depicts a general approach to modify any protein or antibody into a stable protein or antibody, according to an embodiment of the present invention.

FIG. 1 depicts a general approach 10 to modify any antibody, e.g. a native antibody. In one embodiment, four solutions may be required to produce an antibody ionic liquid: a solution of antibodies 12, a solution of cationic crosslinker molecules 14, a solution of coupling agents 16, and a corresponding anion 18. The anion 18 may be biologically-derived or abiotic. The examples presented herein utilize biologically-derived anions, but abiotic anions may be used in the same manner. After the antibodies 12 are cationized (cationized antibodies 20 with cationic crosslinker molecules depicted as "+"), biologically-derived (or biologically-compatible) anions 18 are combined with the cationized antibodies 20 to form an antibody/anion salt 22. Removal of all or most of the water, i.e. at least 95% or at least 99%, results in an ultra-stable antibody ionic liquid 24, which is depicted in a sample tube. The antibody ionic liquid 24 may require no refrigeration, may be stable at room temperature, and may be stable up to about 200° C.

Figure 2:
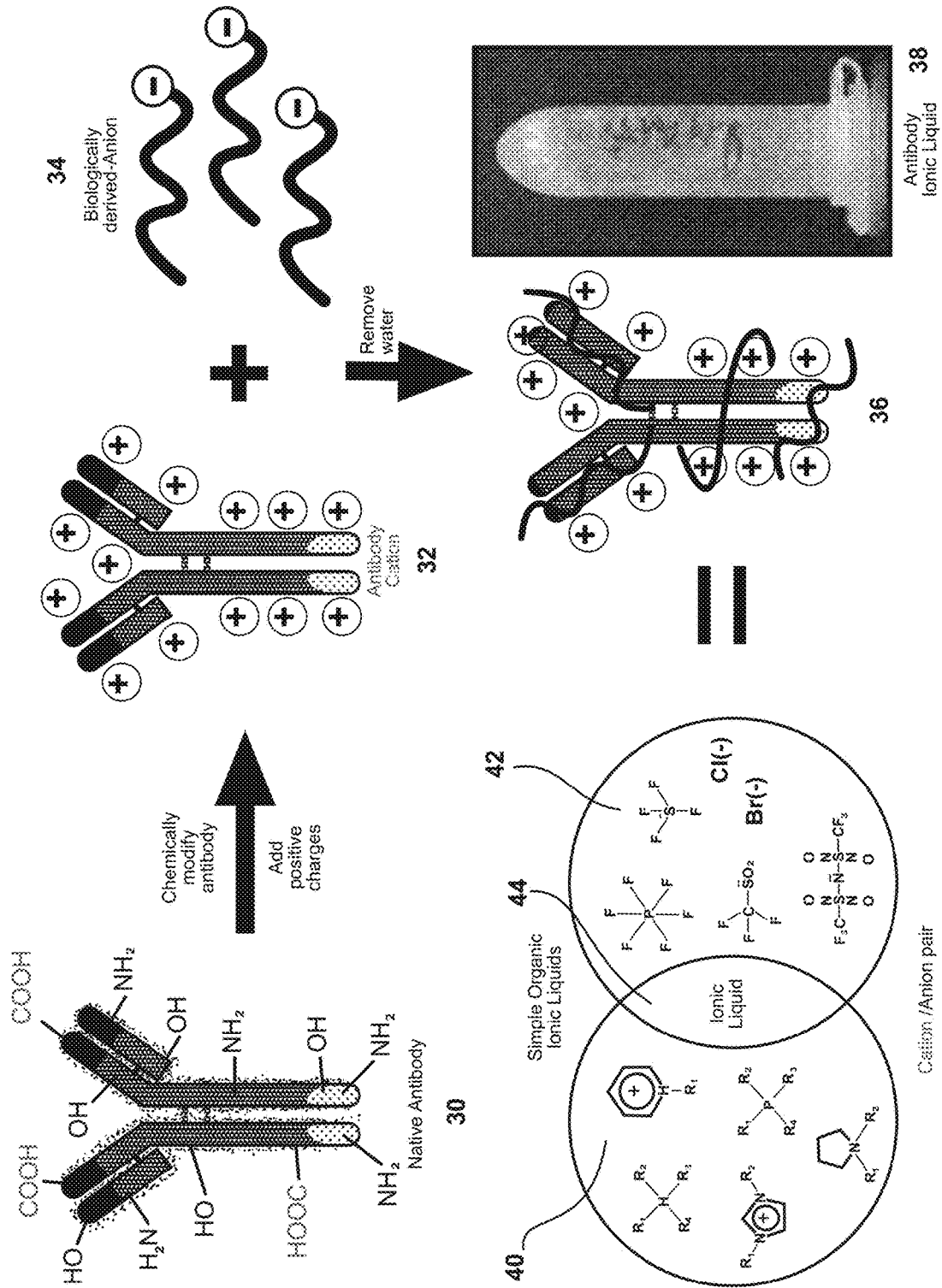
FIG. 2 depicts a more-detailed approach to modify any protein or antibody into a stable protein or antibody, according to an embodiment of the present invention.

FIG. 2 depicts another embodiment of the invention to modify any antibody. Some of the numerous acidic sites, i.e., —COOH (carboxyl), basic sites —NH$_2$ (amine), and neutral sites —OH (hydroxyl) are depicted on a native (unmodified) antibody 30. At least some of the carboxyl, amine and hydroxyl groups may be modified in order to achieve a cationic antibody 32, i.e. the carboxyl, amine and hydroxyl groups (depicted on native antibody 30) of the native antibody 30 are negative sites which tend to make the native antibody 30 generally anionic. This may be done selectively. Various cations may be used to selectively modify the carboxyl, amine and hydroxyl groups. For example, EDC (1-ethyl-3-(3-dimethylaminopropyl) carbodiimide) may be used to modify the carboxyl groups, SIA (succinimidyl iodoacetate) may be used to modify the amine groups, and PMPI (N-(p-maleimidophenyl) isocyanate) may be used to modify the hydroxyl groups (not shown) to form an antibody cation 32. Cations in FIG. 32 are represented by "+". If only a fraction of each carboxyl, amine and hydroxyl group is desired to be modified, in order to maintain the functionality of the antibody salt, the stoichiometry may be adjusted to limit the reagents (e.g., EDC, SIA, PMPI) and thereby limit the number of groups, i.e. the carboxyl, amine and hydroxyl groups, which are modified. After the antibody is cationized 32, the cationized antibody 32 may be combined with an anion 34 in order to form an antibody ionic liquid 36 after removal of most of the water. The antibody ionic liquid 36 is depicted in a sample tube 38.

Figure 3:
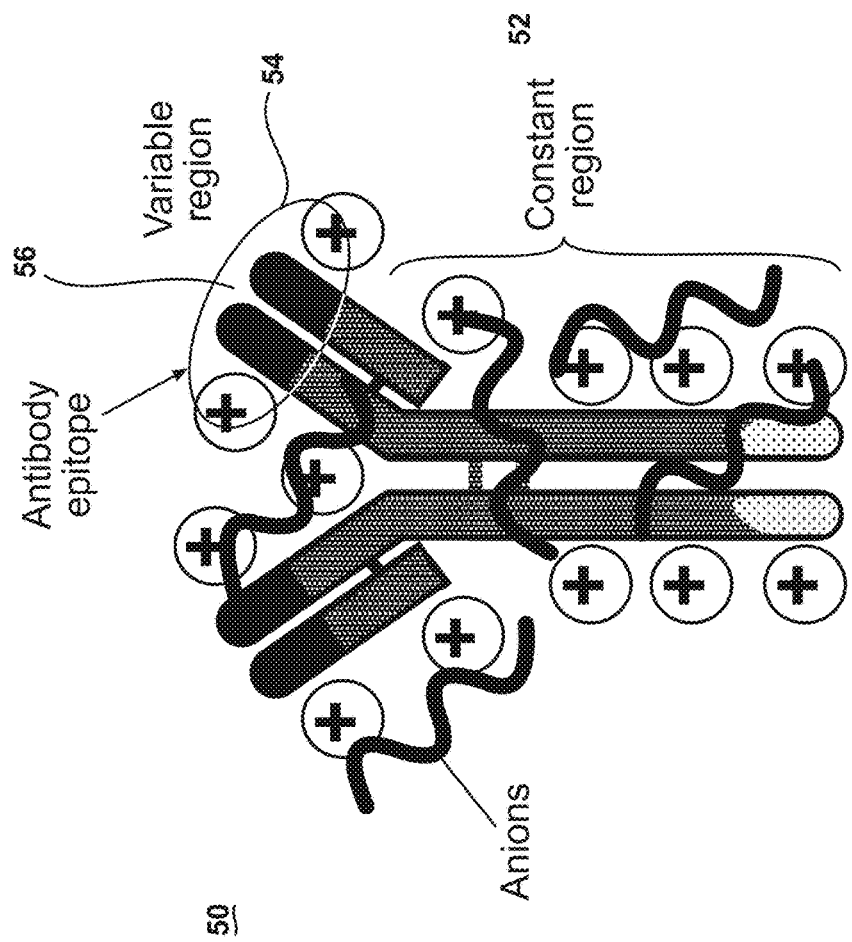
FIG. 3 depicts a typical protein or antibody that has been cationized, according to the present invention.

FIG. 3 depicts a typical antibody 50 that has been cationized. A typical antibody 50 has a constant region 52 and a variable region 54. The constant region 52 (corresponding to about the lower two-thirds of the depicted antibody 50) is generally the same for antibodies. The variable region 54, depicted as the upper ends of the Y branches, includes an antibody epitope 56 which will be distinct for each different type of antibody, depending on its affinity for a specific antigen. This gives the antigen its functionality. In one embodiment, only the constant region 52 is modified so as to retain the functionality of the antigen 50. Even with fewer than only about 5-15% of the amino acids in the constant region 52 modified taking into account the total number of amino acids in the constant region, or about 60-90% of the negative sites in the constant region, the resulting antibody ionic liquid will exhibit binding affinity and functionality with appropriate antigens.

Figure 4:
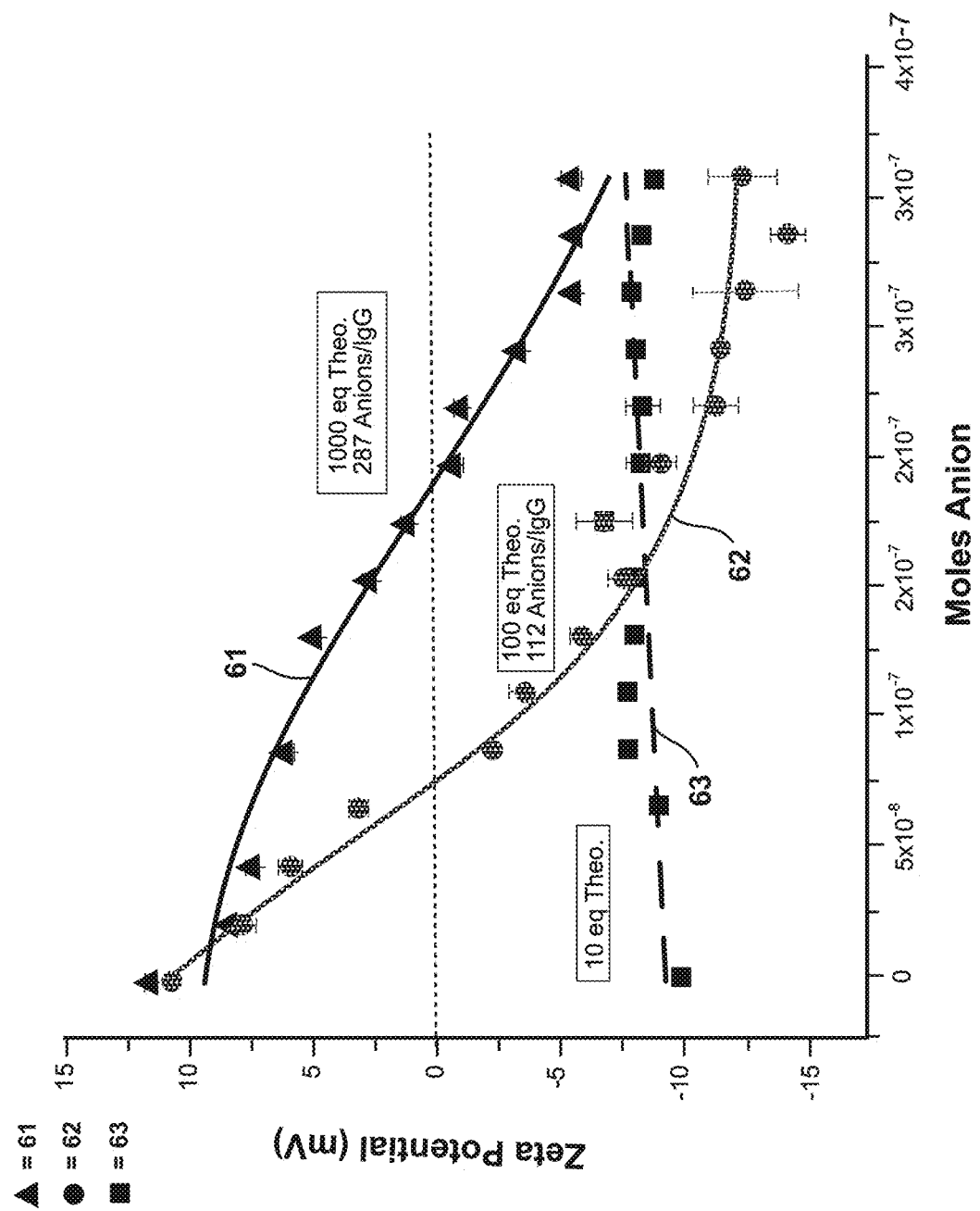
FIG. 4 depicts the cationization of a protein or antibody solution in the presence of a coupling agent, according to an embodiment of the present invention.

FIG. 4 depicts the cationization of an antibody solution in the presence of a coupling agent. In one embodiment, cationization gives the antibody a positive charge without neutralizing its functionality. Too few positive charges means the antibody will not form an ionic liquid with an anion. Too many positive charges may result in the antibody losing its functionality. FIG. 4 graphically illustrates how the concentrations of the coupling agents may affect the overall charge of the antibodies, and accordingly, about how many anions will be bound with the cationic antibodies. There are about 144 acidic amino acids on a typical antibody, and about 1600 total (acidic and non-acidic) amino acids. The non-acidic amino acids control the functionality of the antibodies. If too many (more than about 30% of the total amino acids) non-acid amino acids are coupled the antibody loses its specificity and affinity, i.e. it no longer functions as an antibody. The chart of FIG. 4 illustrates that there is a practical limit as to how many anions may be bound by a cationic antibody. The dashed line (line 63 with square data points) illustrates a cationic antibody solution that has been cationized at about 10 equivalents (theoretic—about 10 positive charges per IgG antibody) based on the strength of the coupling agents. Line 63 starts with a negative zeta potential, which indicates that the cationization was insufficient to give the antibodies a positive charge overall. Thus this low level of cationization is insufficient for use in making an antibody ionic liquid.

Line 62 (solid line with circle data points) illustrates a cationic antibody solution that has been cationized at about 100 equivalents (theoretic) based on the strength of the coupling agents. Line 62 starts with a positive zeta potential, which indicates that the cationization was sufficient to give the antibodies a positive charge overall. Thus this level of cationization is sufficient for use in making an antibody ionic liquid. Likewise, line 61 (solid line with triangle data points) illustrates a cationic antibody solution that has been cationized at about 1000 equivalents (theoretic) based on the strength of the coupling agents. Line 61 starts with a positive zeta potential, which indicates that the cationization was sufficient to give the antibodies a positive charge overall. Thus this level of cationization is also sufficient for use in making an antibody ionic liquid. However, the extra strength of the coupling agents did not affect the formation of the ionic liquid to the degree expected from the concentration of the coupling agents.

Figure 5:
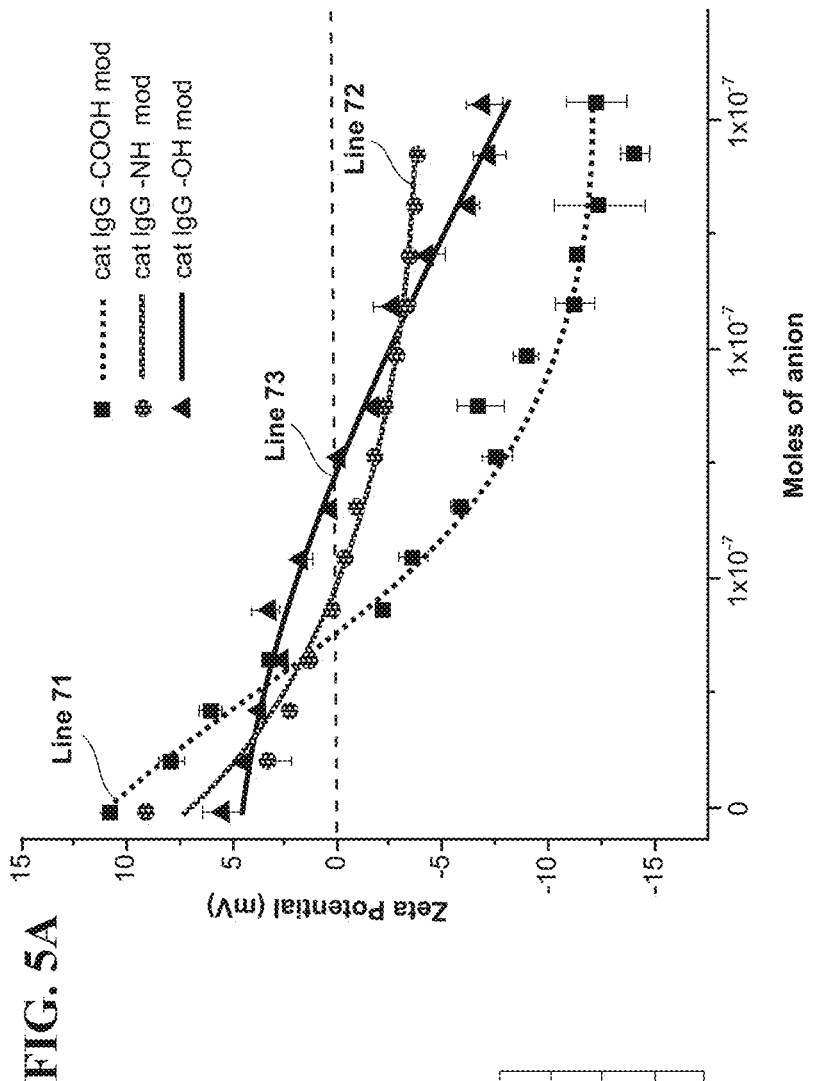
FIGS. 5A-5B depict the selective cationization of IgG in the presence of coupling agents, according to an embodiment of the present invention.

FIG. 5A depicts another embodiment of the invention with the selective cationization of immunoglobulin (IgG) in the presence of coupling agents. There are different numbers of the carboxyl, amine and hydroxyl groups in a typical antibody. These may be selectively coupled through the use of particular coupling agents, including, for example, SIA, PMPI, AMAS (N-α-maleimidoacet-oxysuccinimide ester), BMPS (N-β-maleimidopropyl-oxysuccinimide), SBAP (succinimidy 3-(bromoacetamido) propionate), a photoactive coupling agent (e.g. ANB-NOS (N-5-azido-2-nitrobenzoylsuccinimide) or sulfo-SDA (sulfosuccinimidyl-4,4'-azipentanoate)), or BMPH (N-β-maleimidopropionic acid hydrazide), and combinations thereof. AMAS, BMPS or SBAP may be used as a substitute for SIA. For example, SIA may be used to cationize the amine ($-NH_2$) sites, and PMPI may be used to cationize the hydroxyl ($-OH$) groups. Selective cationization of these groups in the antibodies may be accomplished with selected coupling agents, and/or the use of selected coupling agents as limited reagents, in order to achieve a desired cationic state or positive zeta potential. Line 71 (line with square data points) corresponds to the cationization of carboxyl ($-COOH$) groups, line 72 (line with circular data points) corresponds to the cationization of amine ($-NH$) groups), and line 73 (line with triangular data points) corresponds to the cationization of hydroxyl ($-OH$) groups). In one embodiment of the present invention, each of these groups may be selectively and/or partially cationized to achieve the desire cationic state or zeta potential in order to function properly as an ionic liquid. FIG. 5B illustrates a comparison between the theoretical total number of amino acid groups ($-COOH$ or $NH_2$ or $-OH$) which may be modified with a positive charge and the actual number that were modified in a particular experiment. Out of a total of 144 $-COOH$ groups (corresponding to line 1 of the graph presented on FIG. 5A), 115 of those were modified, leaving 29 $-COOH$ groups unmodified.

Figure 6:
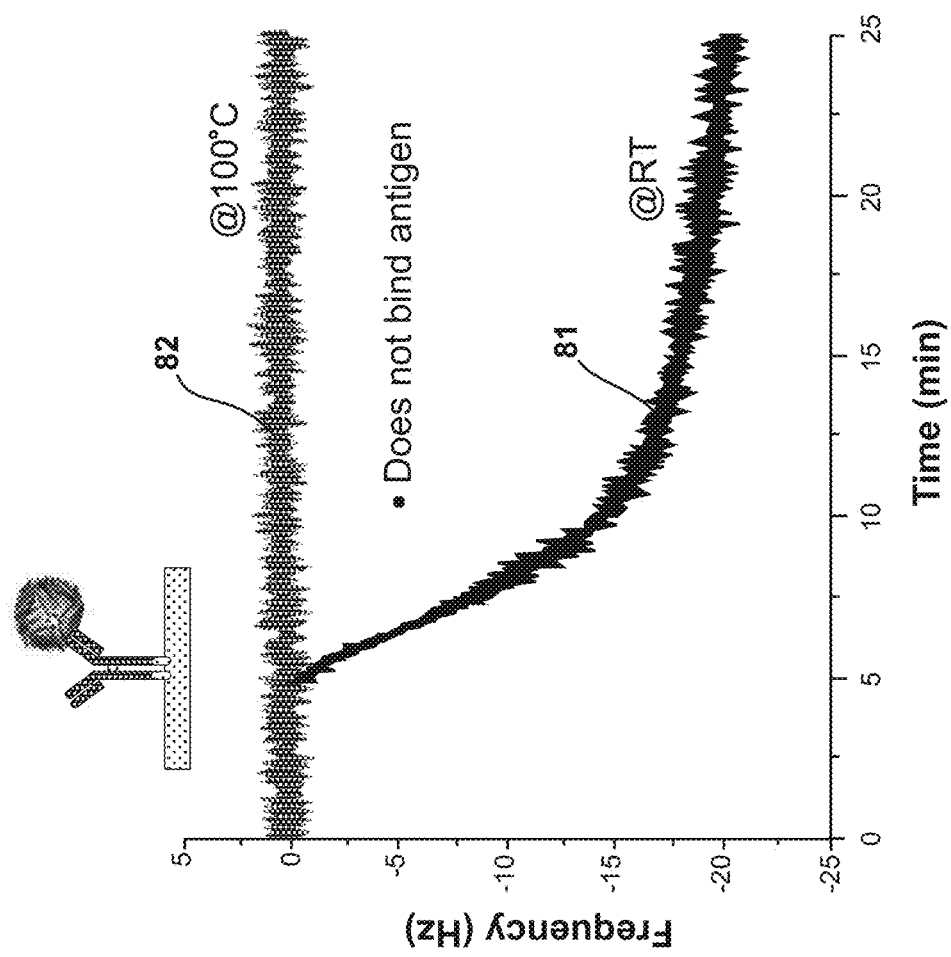
FIG. 6 depicts the antigen binding of an aqueous antibody at room temperature and at 100° C., according to an embodiment of the present invention.

FIG. 6 depicts the antigen binding of an aqueous antibody at room temperature (i.e. about 21-25° C.) 81 and at 100° C. 82 using a quartz crystal microbalance (QCM) to measure mass of antigen adsorbed to an antibody immobilized quartz sensor. FIG. 6 illustrates that an aqueous antibody solution cannot handle elevated temperatures, as is depicted by the change in frequency response as temperature increases. As the temperature increases to 100° C., the antibody solution exhibits decreasing binding activity until no binding activity is seen. That is, no binding is observed when a constant frequency value of 0 Hz+/−0.5 Hz over time is measured.

Figure 7:
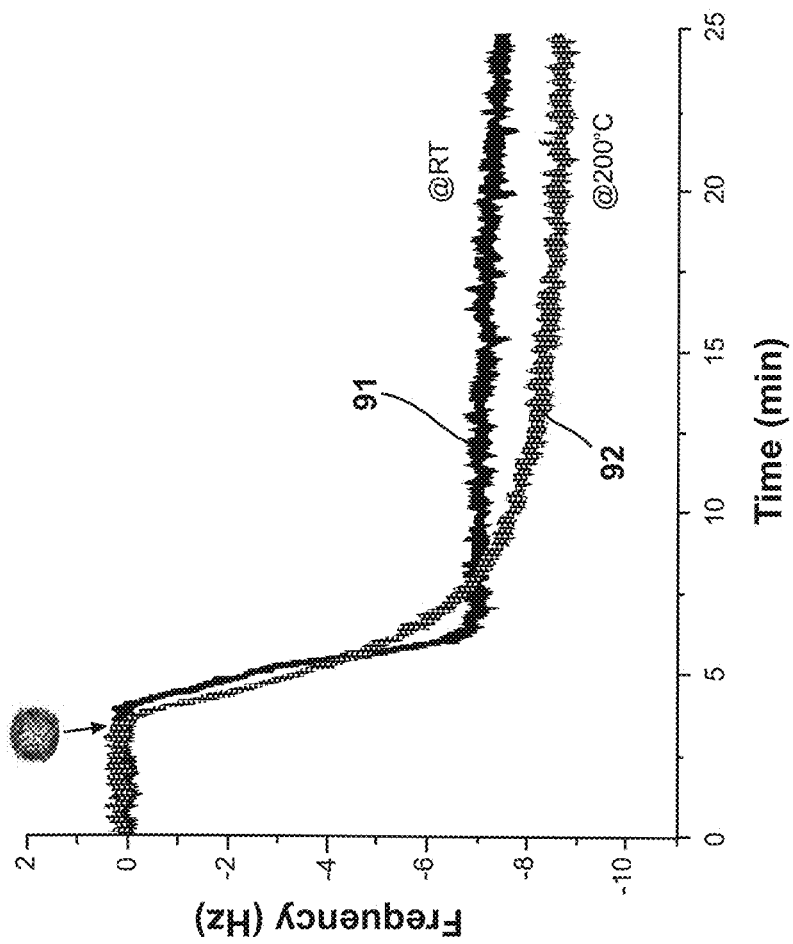
FIG. 7 depicts the antigen binding of an ionic liquid antibody at room temperature and at 200° C., according to an embodiment of the present invention.

FIG. 7 depicts the antigen binding of an ionic liquid antibody at room temperature (i.e. about 21-25° C.) 91 and at 200° C. 92 using a quartz crystal microbalance to measure mass of antigen adsorbed to an antibody immobilized quartz sensor. Binding is observed when the frequency decreases by more than about 2 Hz over time and a clear slope is observed vs. the initial baseline before antigen is added. FIG. 7 illustrates that an ionic liquid antibody solution can handle elevated temperatures and maintains functionality, as is depicted by the change in frequency response as temperature increases. As the temperature increases to 200° C., the antibody ionic liquid continues to exhibit binding activity similar to its performance at room temperature.

Numerous anions were identified as possibilities for making an antibody liquid salt. However, non-biological polymer anions may trigger an immune response if used in vivo. A few biological anions were discovered to be amenable to making protein ionic liquids, including DL-lactate, linolenate, phospholipids, fatty acids, and combinations thereof, which are biocompatible. These are presented only as examples and the invention is not intended to be limited solely to those biological anions. Any biologically-derived anion with a low melting point (e.g. between about 5-30° C.) that known in the art may be used. The same methodology is generally applicable to all antibodies and yields antibody ionic liquids which are stable and maintain efficacy up to 200° C., as illustrated in FIG. 7.

In one embodiment, creation of a water-free ultra-stable antibody ionic liquid, aqueous anti-hemoglobin antibodies produced in rabbits were cationized by addition of stoichiometric amounts of N,N-dimethyl-1,3-propanediamine in the presence of 1-ethyl-3-(3-dimethylaminopropyl) carbodiimide (EDC) coupling reagent; addition of succinimidyl iodoacetate (SIA) and 2-(dimethylamino) ethanethiol, and/or N-(p-maleimidophenyl) isocyanate (PMPI) and 2-(dimethylamino) ethanethiol. After cationization, the cationized antibodies were purified from excess coupling reagents by repeated dialysis in water using dialysis membranes with molecular weight cutoffs (MWCO) of 7000 g/mol. Cationized antibodies were confirmed by a positive zeta potential value.

Next, cationized antibodies were titrated with a corresponding non-toxic and bio-compatible counter anionic polymer of $C_9H_9C_6H_4-(OCH_2CH_2)_{20}O(CH_2)_3SO_3$ until positive charges on antibody became slightly negative by zeta potential measurements.

The antibody cation/anion pair was dialyzed repeatedly in water to remove excess anionic polymer using MWCO 7000 dialysis membranes and lyophilized to remove enough water.

Finally, lyophilized solid, e.g. powder, of the cationized anti-hemoglobin/anion pair was slowly, e.g. over a 20-minute period or more, heated to about 50° C. until a viscous clear liquid was generated. In one embodiment, the heating period is 30-90 minutes. In another embodiment, the cationized anti-hemoglobin pair is heated to 40-90° C. The anti-hemoglobin antibody ionic liquids were tested for antibody recognition of hemoglobin antigen using a dot blot assay on a nitrocellulose membrane and after heating at about 100° C. for 2 hours to test for temperature resistance. The antibody ionic liquid had retained its functionality.

The resulting antibody ionic liquids are ultra-stable, possess long shelf-lives (i.e. greater than about 5 years), do not require refrigeration for storage/handling/use, do not have to adhere to a cold supply chain, are resistant to extreme temperatures (such as temperatures greater than about 100° C.), are non-toxic and biologically compatible, and can be easily reconstituted into water or a biological buffer for therapeutic use. By comparison, antibodies in aqueous solutions have limited shelf-lives even with controlled refrigeration, are extremely sensitive to increased temperatures, and quickly lose all biological recognition activity. In one embodiment, antibody ionic liquids provided by the disclosed method may reduce costs associated with refrigeration and may also eliminate the substantial weight burden of heavy refrigeration equipment.

In one embodiment, water-free antibody liquids may also be prepared with stable single chain antibodies from camelids, antibody fragments, or may contain combinations of multiple antibodies to create multi-recognition antibody liquids.

Ultra-stable antibody liquids may permit refrigeration-free handling, storage and antibody-based diagnostics. They are resistant to extreme temperatures, have long shelf lives (e.g. a 20-fold improvement of the prior art), reduce the cost/weight load of specialized refrigeration equipment, and are able to be transported to underdeveloped countries while maintaining efficacy.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. A stable protein ionic liquid, comprising:
   an anti-hemoglobin cation/anion pair, wherein the anti-hemoglobin cation/anion pair is:
   an anionic polymer of poly(ethylene glycol) 4-nonylphenyl 3-sulfopropyl ether.

2. The stable protein ionic liquid of claim 1, wherein the anti-hemoglobin cation/anion pair further comprises:
   a cationized anti-hemoglobin antibody, a single-chain antibody from camelids, antibody fragments, a polyclonal Anti-horse spleen ferritin antibody, a monoclonal Anti-Flag antibody, monoclonal Anti-HRP2 to *Plasmodium falciparum*, polyclonal Anti-neuropeptide Y, polyclonal Anti-human troponin, isotypes of antibodies, or a combination thereof.

\* \* \* \* \*